US010342687B2

(12) United States Patent
Kim

(10) Patent No.: US 10,342,687 B2
(45) Date of Patent: Jul. 9, 2019

(54) APPARATUS AND METHOD FOR INSERTING BRANCH STENT

(71) Applicant: Junghoon Kim, Bothell, WA (US)

(72) Inventor: Junghoon Kim, Bothell, WA (US)

(73) Assignee: Junghoon Kim, Bothell, WA (US)

( * ) Notice: Subject to any disclaimer, the term of this patent is extended or adjusted under 35 U.S.C. 154(b) by 0 days.

(21) Appl. No.: 15/613,657

(22) Filed: Jun. 5, 2017

(65) Prior Publication Data

US 2018/0344492 A1 Dec. 6, 2018

(51) Int. Cl.
*A61F 2/06* (2013.01)
*A61F 2/954* (2013.01)
*A61F 2/95* (2013.01)

(52) U.S. Cl.
CPC ........ *A61F 2/954* (2013.01); *A61F 2002/065* (2013.01); *A61F 2002/9517* (2013.01); *A61F 2230/0006* (2013.01); *A61F 2230/0017* (2013.01); *A61F 2230/0019* (2013.01)

(58) Field of Classification Search
CPC .. A61F 2/95; A61F 2/954; A61F 2/962; A61F 2/06; A61F 2/07; A61F 2/88; A61F 2/90; A61F 2/91; A61F 2/82
See application file for complete search history.

(56) References Cited

U.S. PATENT DOCUMENTS

| 5,639,278 | A | * | 6/1997 | Dereume | ................. | A61F 2/07 |
| | | | | | | 623/1.13 |
| 6,086,611 | A | | 7/2000 | Duffy et al. | | |
| 8,197,536 | B2 | | 6/2012 | Krever et al. | | |
| 2011/0307049 | A1 | * | 12/2011 | Kao | ....................... | A61F 2/966 |
| | | | | | | 623/1.11 |

FOREIGN PATENT DOCUMENTS

| JP | 2007512909 | 5/2007 |
| JP | 2008514266 | 5/2008 |
| JP | 2015529500 | 10/2015 |
| KR | 20120035978 | 4/2012 |
| KR | 20140054032 | 5/2014 |

OTHER PUBLICATIONS

International Search Report—PCT/KR2018/006016 dated Sep. 20, 2018.

* cited by examiner

Primary Examiner — Vi X Nguyen
(74) Attorney, Agent, or Firm — Cantor Colburn LLP

(57) ABSTRACT

Provided herein are an apparatus and method for inserting a branch stent. A plurality of insertion guide rods for being delivered to a vascular or non-vascular bifurcation to which a stent expansion wire is connected are configured in an insert tube. In this way, a branch stent can be immediately delivered to the vascular or non-vascular bifurcation and expanded through just one operation so that an operation related to the branch stent is conveniently and promptly performed.

6 Claims, 9 Drawing Sheets

APPARATUS AND METHOD FOR INSERTING BRANCH STENT

BACKGROUND

1. Field of the Invention

The present disclosure relates to an apparatus for inserting a branch stent capable of stably delivering and expanding a branch stent to all organs including a branch vessel or a non-vascular organ in the human body.

2. Discussion of Related Art

Generally, a stent placement method is used to artificially widen a location of stenosis is inserted. When stenosis occurs due to causes such as sediment and a tumor tissue in a vessel or a non-vascular organ such as esophagus, bile duct, bronchus, and urethra which requires to secure a certain diameter.

Nowadays, a method of placing a stent for several times at intervals at a vascular or non-vascular bifurcation formed in a Y-shape inside the human body is being tried.

However, it is complicated to perform stent placement for several times at intervals. To improve success rate an expansion system in which a branch catheter having a joint is inserted into a vascular or non-vascular bifurcation by using a wire in two standard vessels or non-vessels. Then a branch stent is inserted into the branch catheter by using a stent expansion wire and allows, an electrical signal to be applied to the branch catheter so that the joint is divided, and the branch catheter is to be removed from the vascular or non-vascular bifurcation. It allows the branch stent to be exposed and automatically expanded in the vascular or non-vascular bifurcation has been provided.

However, the method of realizing the expansion system is complicated.

The complicated operation process in which a branch stent is automatically expanded in a vascular or non-vascular bifurcation is performed only through a first step in which a branch catheter is inserted into the vascular or non-vascular bifurcation, a second step in which the branch stent is inserted into the branch catheter, a third step in which a joint of the branch stent is divided by an electrical signal, and a fourth step in which the branch stent is separated from the vascular or non-vascular bifurcation.

SUMMARY OF THE INVENTION

The present disclosure has been made in view of the above problems, and the main objective of the present disclosure is to provide an apparatus for inserting a branch stent capable of immediately delivering and expanding the branch stent to a vascular or non-vascular bifurcation through only one operation.

To achieve the above objective, the apparatus for inserting a branch stent according to the present disclosure includes an insert tube inserted into an entry duct of a vessel or non-vessel, a plurality of insertion guide rods disposed in the insert tube, and a plurality of stent inserting parts each having one end connected to the plurality of insertion guide rods and the other end connected to an operation handle and configured to selectively insert the insertion guide rod into first and second branch ducts branched from the entry duct of the vessel or non-vessel, wherein a branch stent that is automatically expanded in the entry duct and the first and second branch ducts when the insertion guide rod is deviated from the insert tube and inserted into the first and second branch ducts is coupled to the stent inserting part.

The insert tube may be circular shape, a semi-spherical shape, or a polygonal shape.

The insertion guide rod may include a tubular body part, a first fixing part formed at an outer peripheral surface of the other end of the tubular body part and configured to press and fix the one end of the stent inserting part when the one end of the stent inserting part is inserted into the other end of the tubular body part, and a cover part formed at one end of the tubular body part and configured to guide insertion of the tubular body part into the first and second branch ducts.

The cover part may be formed in an inclined structure in which a diameter is gradually decreased from a rear end side inserted into the one end of the tubular body part towards a front end side.

The tubular body part may be a tube of a circular shape, a semi-spherical shape, or a polygonal shape.

The branch stent may be coupled to surround the stent is inserting part and include a main stent and first and second branch stents branched from the main stent.

The first and second branch stents may automatically be expanded when deviated from the insert tube from a state of overlapping the insert tube and being pressed therein.

According to another aspect, a method for inserting a branch stent includes (a) inserting an insert tube into an entry duct of a vessel or non-vessel; (b) exposing a part of the branch stent while deviating a plurality of insertion guide rods from the insert tube by using a plurality of handles; (c) advancing one insertion guide rod and a stent inserting part connected thereto toward a second branch duct of a vessel or non-vessel by using one operation handle to automatically expand a second branch stent of the branch stent in the second branch duct; (d) advancing the other insertion guide rod and a stent inserting part connected thereto toward a first branch duct of a vessel or non-vessel by using the other operation handle to automatically expand the entry duct as well as a main stent and a first branch stent in the first branch duct; and (e) removing the insert tube and the insertion guide rods from the entry duct of a vessel or non-vessel and the first and second branch ducts.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
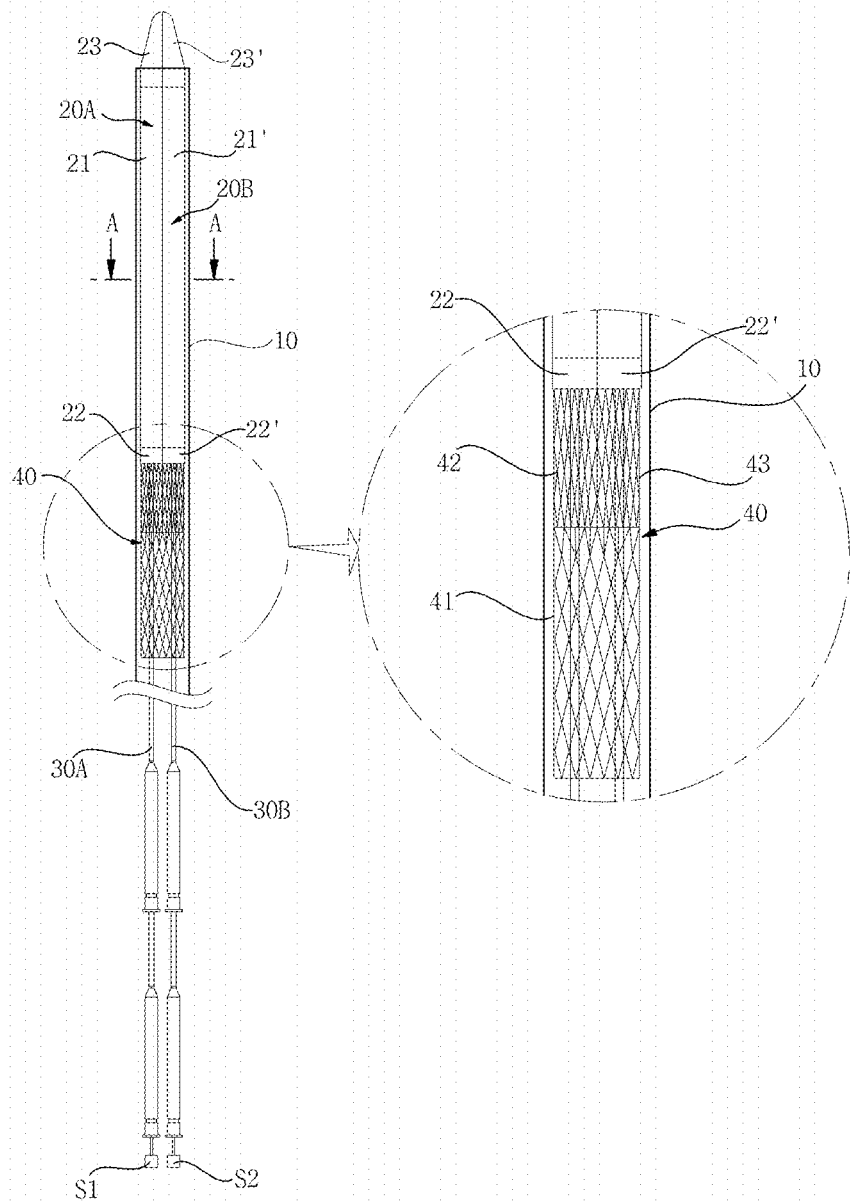
FIG. 1 is a structural diagram of an apparatus for inserting a branch stent that illustrates a state in which a plurality of insertion guide rods are inserted into an insert tube according to an embodiment of the present disclosure.

Advantages, features, and a method of achieving the same will become clear when referring to embodiments described in detail below with reference to the accompanying drawings. However, embodiments according to the technical spirit of the present disclosure are not limited to the embodiments disclosed below and may be implemented in various different forms. The embodiments herein are provided to make the mere disclosure of the present disclosure complete and inform one of ordinary skills in the art to which the present disclosure pertains of the scope of the disclosure. The scope of the embodiments according to the technical spirit of the present disclosure is defined only by the scope of the claims.

Terms herein used are for describing the embodiments and are not intended to limit the present disclosure. In the application, a singular expression includes a plurality expression unless the context clearly indicated otherwise.

In the application, terms such as "include" or "have" should be understood as designating the features, number, steps, operations, elements, parts, or combinations thereof exist and not as precluding the existence of or the possibility of adding one or more other features, numbers, steps, operations, elements, parts, or combinations thereof in advance.

In addition, the embodiments described herein is described with reference to cross-sectional views and/or plan views which are ideal exemplary views of the present disclosure. Therefore, the embodiments of the present disclosure are not limited to specific illustrated forms but also include modifications of required forms. For example, an area illustrated to be right-angled may also have a rounded form or a form having a predetermined curvature. Therefore, areas illustrated in the drawings have schematic characteristics. The shapes of the areas illustrated in the drawings are for exemplifying specific forms of the areas and are not intended to limit the scope of the disclosure.

Like reference numerals refer to like elements throughout. Although not mentioned or described with reference to a corresponding drawing, like reference numerals or similar reference numerals may be described with reference to another drawing. Similarly, reference numerals are not marked in a corresponding drawing drawings, the reference numerals may be described with reference to another drawing.

Hereinafter, embodiments of the present disclosure will be described with reference to the accompanying drawings.

Figure 2:
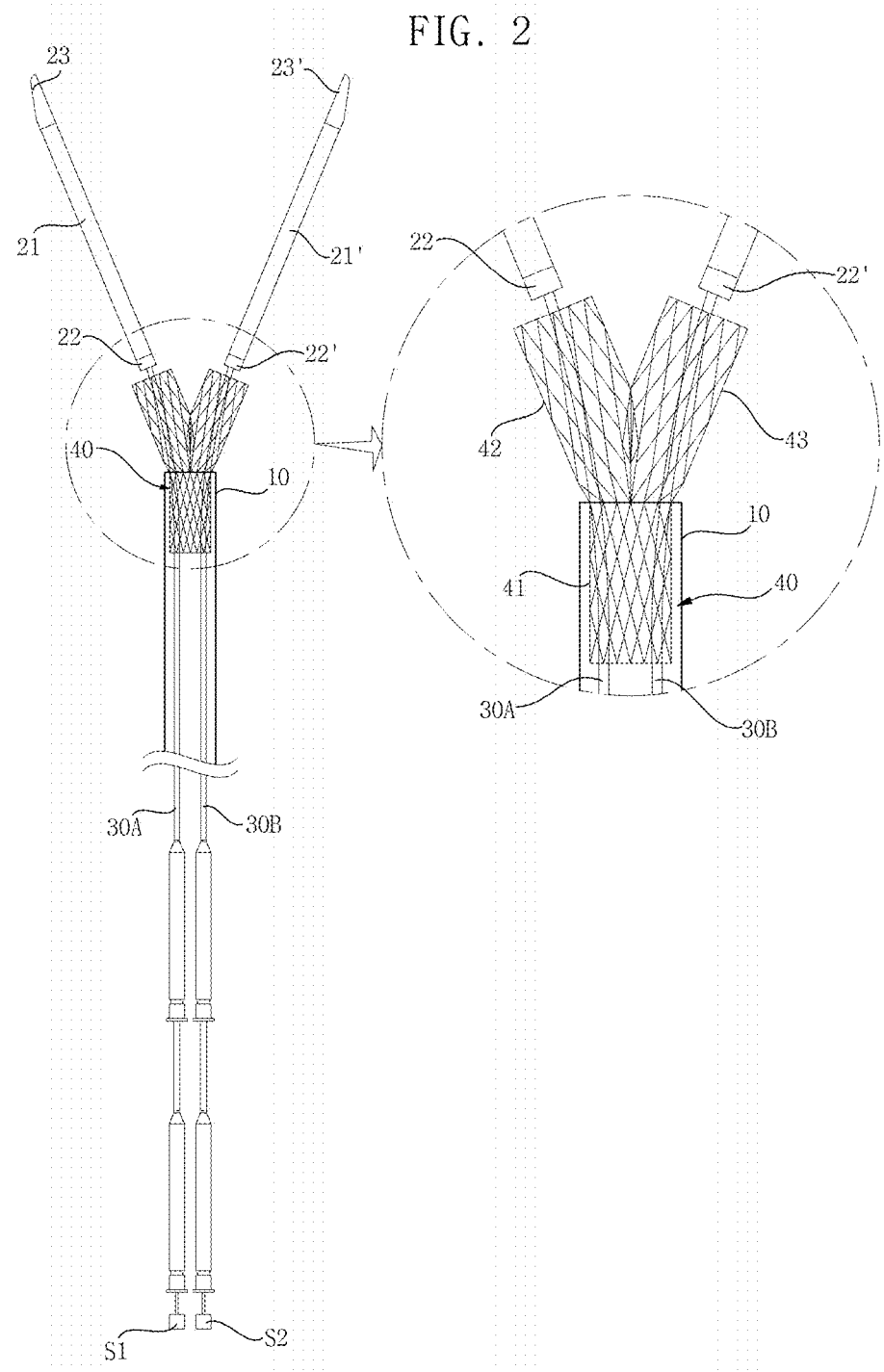
FIG. 2 is a structural diagram of the apparatus for inserting a branch stent that illustrates a state in which the plurality of insertion guide rods are withdrawn from the insert tube according to an embodiment of the present disclosure.

FIG. 1 is a structural diagram of an apparatus for inserting a branch stent illustrating a state in which a plurality of insertion guide rods are inserted into an insert tube according to an embodiment of the present disclosure. FIG. 2 is a structural diagram of the apparatus for inserting a branch stent illustrating a state in which the plurality of insertion guide rods are withdrawn from the insert tube according to an embodiment of the present disclosure.

Referring to FIGS. 1 and 2, an apparatus for inserting a branch stent according to an embodiment of the present disclosure is applied to an operation in which a stent is stably placed in a vessel or non-vessel, when various vessels or non-vessels formed in the human body are branched into a plurality of vessels or non-vessels and when a plurality of vessels or non-vessels are combined into one vessel or non-vessel. That is, the apparatus for inserting a branch stent can be applied when a vessel such as a cerebral vessel or coronary artery or a non-vessel such as bile duct, ureter, or bronchus are branched into a plurality of vessels or non-vessels or when a plurality of vessels or non-vessels are combined into one vessel or non-vessel, and includes an insert tube 10, a plurality of insertion guide rods 20A and 20B, a plurality of stent inserting parts 30A and 30B, and a branch stent 40.

The insert tube 10 is configured to be inserted into a vessel or non-vessel. Any one of a circular tube with a hollow, a semi-spherical tube illustrated in FIG. 8, a hexagonal tube illustrated as a polygonal shape in FIG. 9, a triangular tube illustrated in FIG. 10, and a rectangular tube illustrated in FIG. 11 may be applied as the insert tube 10.

Figure 9:
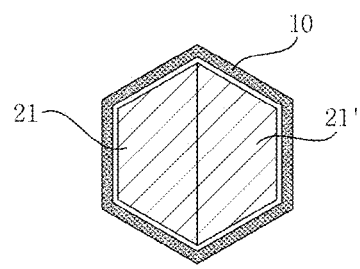
FIG. 9 is a cross-sectional view taken along line A-A in FIG. 1 illustrating a hexagonal insertion guide rod according to another embodiment of the present disclosure.
Figure 10:
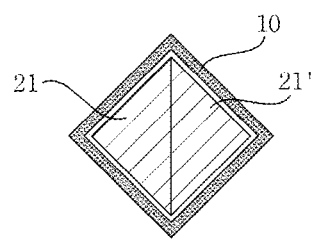
FIG. 10 is a cross-sectional view taken along line A-A in FIG. 1 illustrating a triangular insertion guide rod according to another embodiment of the present disclosure.
Figure 11:
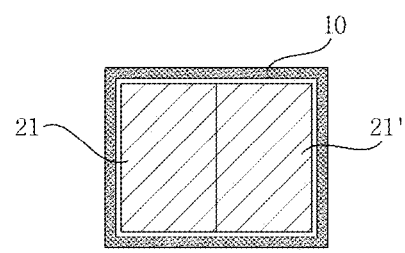
FIG. 11 is a cross-sectional view taken along line A-A in FIG. 1 illustrating a rectangular insertion guide rod according to another embodiment of the present disclosure.

Although examples of polygonal shapes of the insert tube 10 illustrated in FIGS. 9 to 11 have been described, the shapes of the insert tube 10 are not necessarily limited thereto, and the types of polygonal shapes may be modified in various ways as needed.

The insertion guide rods 20A and 20B may be disposed in the insert tube 10. The insertion guide rods 20A and 20B are formed of structures having the same shape. The insertion guide rods 20A and 20B are configured to be respectively inserted into a first branch duct 101 and a second branch duct 102 branched from an entry duct 100 of a vessel or non-vessel and include tubular body parts 21 and 21', first fixing parts 22 and 22', and cover parts 23 and 23'.

The tubular body parts 21 and 21' are circular tubes, semi-spherical tubes, or polygonal tubes with a hollow.

Figure 8:
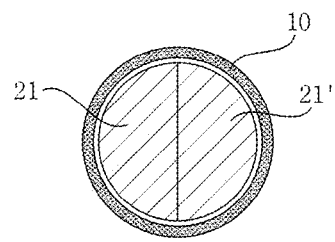
FIG. 8 is a cross-sectional view taken along line A-A in FIG. 1 illustrating a semi-spherical insertion guide rod according to an embodiment of the present disclosure.

That is, any one of the circular tube with a hollow, the semi-spherical tube illustrated in FIG. 8, the hexagonal tube illustrated as a polygonal shape in FIG. 9, the triangular tube illustrated in FIG. 10, and the rectangular tube illustrated in FIG. 11 may be applied as the tubular body parts 21 and 21'.

The first fixing parts 22 and 22' are formed at outer peripheral surfaces of the other ends of the tubular body parts 21 and 21'. The first fixing parts 22 and 22' are configured to press and fix one ends of the stent inserting parts 30A and 30B when the one ends of the stent inserting parts 30A and 30B are inserted into the other ends of the tubular body parts 21 and 21'.

The cover parts 23 and 23' are formed at one ends of the tubular body parts 21 and 21'. The cover parts 23 and 23' are configured to guide insertion of the tubular body parts 21 and 21' into the first branch duct 101 and the second branch duct 102 branched from the entry duct 100 of the vessel or non-vessel.

That is, the cover parts 23 and 23' are formed in an inclined structure in which a diameter is gradually decreased from a rear end side inserted into the one ends of the tubular body parts 21 and 21' toward a front end side. This allows the tubular body parts 21 and 21' to easily enter the first branch duct 101 and/or the second branch duct 102 from the entry duct 100 of the vessel or non-vessel.

The stent inserting parts 30A and 30B are wires and are formed of a structure in which one ends are connected to the plurality of insertion guide rods 20A and 20B, respectively, and the other ends are connected to operation handles S1 and S2, respectively. This allows the insertion guide rods 20A and 20B to be selectively inserted into the first branch duct 101 and the second branch duct 102 branched from the entry duct 100 of the vessel or non-vessel.

The branch stent 40 is formed at an outside of the stent inserting parts 30A and 30B. This is to allow the insertion guide rods 20A and 20B to be automatically expanded in the entry duct 100 of the vessel or non-vessel when deviated from the insert tube 10 and inserted into the first branch duct 101 and the second branch duct 102, respectively.

That is, the branch stent 40 includes a main stent 41 configured to surround the stent inserting parts 30A and 30B, and a first branch stent 42 and a second branch stent 43 branched from the main stent 41. The main stent 41 is pressed in the insert tube 10. The first branch stent 42 and the second branch stent 43 overlap the insert tube 10 and are pressed therein. The main stent 41, the first branch stent 42, and the second branch stent 43 are automatically expanded by being widened when deviated from the insert tube 10.

A method for inserting the branch stent 40 into the first branch duct 101 and the second branch duct 102 branched from the entry duct 100 of the vessel or non-vessel by using the apparatus for inserting a branch stent configured as above will be described below.

First, the branch stent 40 is compressed and inserted into the insert tube 10 to surround the plurality of stent inserting parts 30A and 30B disposed in the insert tube 10. Then, the insertion guide rods 20A and 20B connected to the stent inserting parts 30A and 30B, respectively, are inserted into the front end side of the insert tube 10.

Figure 3:
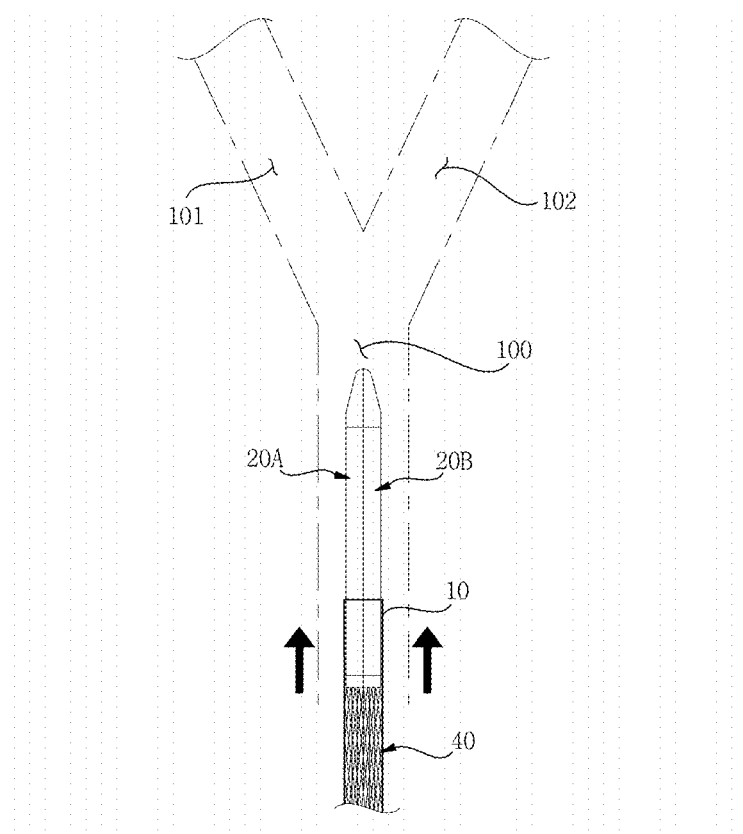
FIG. 3 is a schematic cross-sectional view illustrating a state in which the insert tube is inserted into an entry duct of a vessel or non-vessel according to an embodiment of the present disclosure.

Then, as illustrated in FIG. 3, the insert tube 10 is inserted to be in the vicinity of the first branch duct 101 and the second branch duct 102 branched from the entry duct 100 of the vessel or non-vessel.

Figure 4:
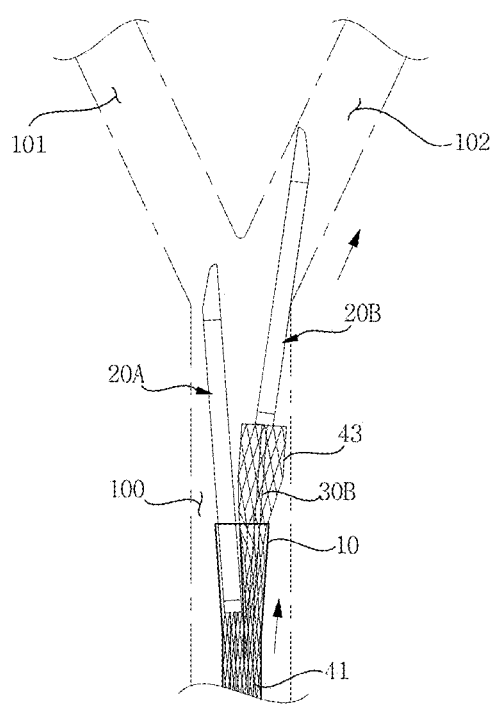
FIG. 4 is a schematic cross-sectional view illustrating a state in which a second branch stent of the branch stent is automatically expanded in a second branch duct of the vessel or non-vessel according to an embodiment of the present disclosure.

Then, as illustrated in FIG. 4, the insertion guide rods 20A and 20B are advanced toward the first branch duct 101 and the second branch duct 102 by using the operation handles S1 and S2 from the outside.

In this way, the insertion guide rods 20A and 20B are deviated from the insert tube 10. By the deviation of the insertion guide rods 20A and 20B, the branch stent 40 disposed in the stent inserting parts 30A and 30B connected to the insertion guide rods 20A and 20B, respectively, is deviated from the insert tube 10 and partially exposed.

Figure 5:
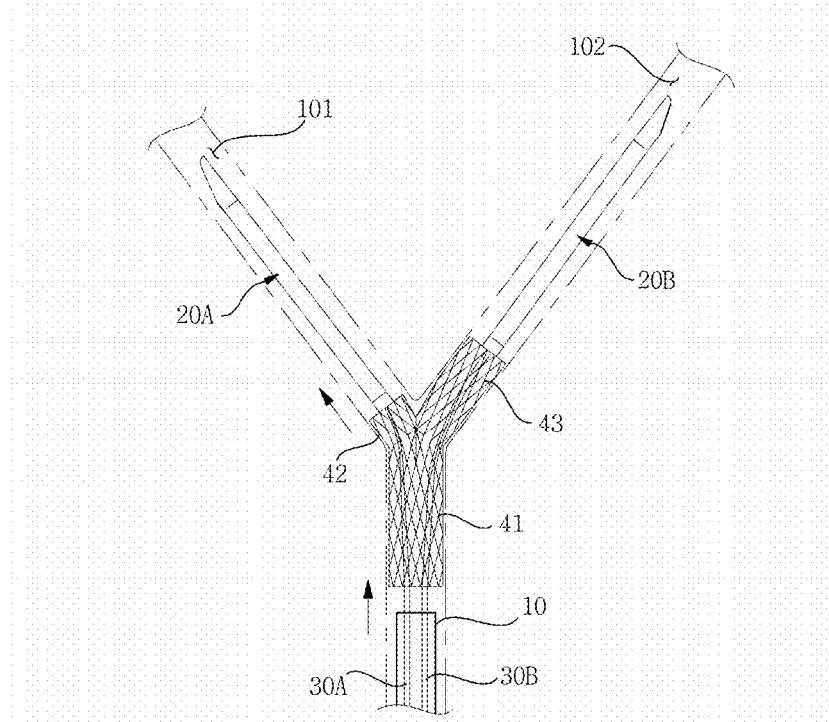
FIG. 5 is a schematic cross-sectional view illustrating a state in which a first branch stent is automatically expanded in a main stent of the branch stent and a first branch duct according to an embodiment of the present disclosure.

Then, as illustrated in FIG. 5, when the branch stent 40 is partially exposed, one insertion guide rod 20B is advanced from the entry duct 100 of the vessel or non-vessel toward the second branch duct 102 by using one operation handle S2. In this way, the second branch stent 43 of the branch stent 40 is exposed and automatically expanded in the second branch duct 102 so that the second branch duct 102 can be widened.

Here, the first branch stent 42 overlaps the second branch step 43. Therefore, when the second branch stent 43 is automatically expanded in the second branch duct 102, the first branch stent 42 is also partially exposed and separated from the second branch stent 43.

Figure 6:
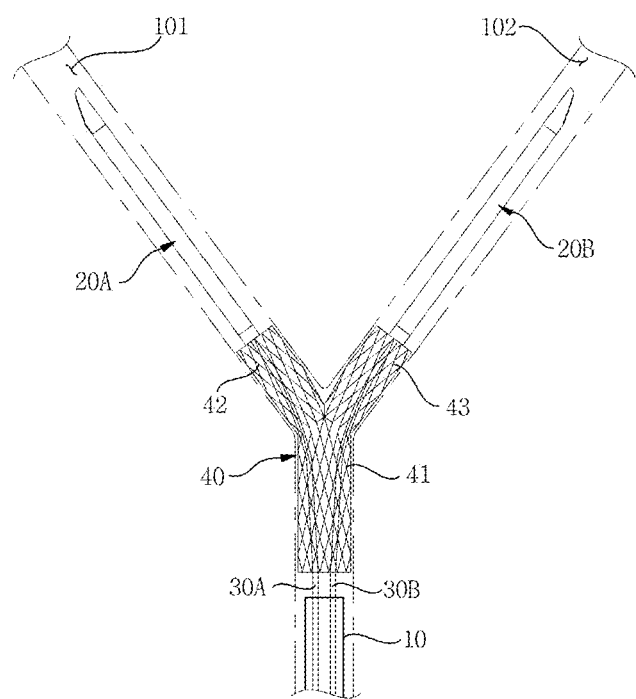
FIG. 6 is a schematic cross-sectional view illustrating a state in which the branch stent is expanded in all of the entry duct of the vessel or non-vessel and the first and second branch ducts according to an embodiment of the present disclosure.

Then, as illustrated in FIG. 6, the other insertion guide rod 20A is advanced from the entry duct 100 of the vessel or non-vessel toward the first branch duct 101 by using the other operation handle S1. In this way, the main stent 41 of the branch stent 40 exposed from the entry duct 100 of the vessel or non-vessel is deviated from the insert tube 10 and automatically expanded. Also, the first branch stent 42 separated from the second branch stent 43 is exposed in the first branch duct 101 and automatically expanded. Consequently, the main stent 41, the first branch stent 42, and the second branch stent 43 of the branch stent 40 widen the entry duct 100 of the vessel or non-vessel as well as the first branch duct 101 and the second branch duct 102 branched from the entry duct 100.

Figure 7:
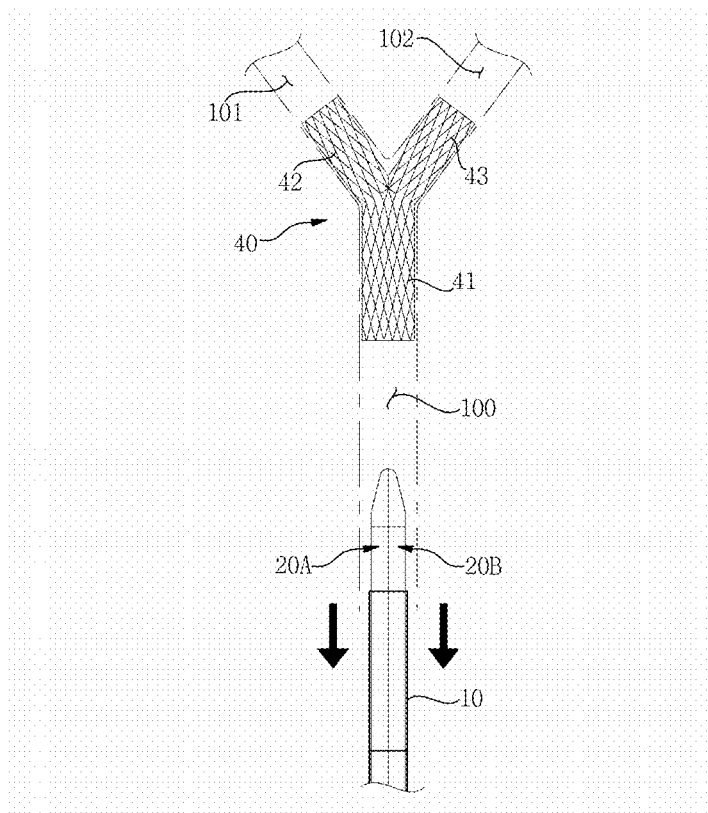
FIG. 7 is a schematic cross-sectional view illustrating a state in which the insert tube and the insertion guide rods are removed from the entry duct of the vessel or non-vessel, and the first and second branch ducts in which the branch stent is expanded according to an embodiment of the present disclosure.

Then, as illustrated in FIG. 7, after the main stent 41, the first branch stent 42, and the second branch stent 43 of the branch stent 40 are automatically expanded, and the entry duct 100 as well as the first branch duct 101 and the second branch duct 102 branched therefrom are widened, the stent insertion operation ends when the insert tube 10 and the insertion guide rods 20A and 20B are removed from the first branch duct 101, the second branch duct 102, and the entry duct 100.

As described above, according to the present disclosure, a plurality of insertion guide rods for being delivered to a vascular or non-vascular bifurcation to which a stent expansion wire is connected are configured in an insert tube. In this way, a branch stent can be immediately delivered to the vascular or non-vascular bifurcation and expanded through just one operation so that an operation related to the branch stent is conveniently and promptly performed.

The advantageous effects of the present disclosure are not limited to those mentioned above, and other unmentioned advantageous effects should be clearly understood by one of ordinary skill in the art from the claims below.

Although the technical spirit of an apparatus and method for inserting a branch stent according to the present disclosure have been described above with reference to the accompanying drawings, optimal embodiments of the present disclosure have been described illustratively and are not intended to limit the present disclosure.

Therefore, the present disclosure is not limited to the specific preferred embodiments described above. One of ordinary skill in the art to which the disclosure pertains may modify and embody the disclosure in various ways without departing from the gist of the present disclosure, and such modifications belong to the scope of the claims below.

What is claimed is:
1. An apparatus for inserting a branch stent, the apparatus comprising:
   an insert tube inserted into an entry duct of a vessel or non-vessel;
   a plurality of insertion guide rods disposed in the insert tube; and
   a plurality of stent inserting parts each having one end connected to the plurality of insertion guide rods and the other end connected to an operation handle and configured to selectively insert the insertion guide rod into first and second branch ducts branched from the entry duct of the vessel or non-vessel, wherein a branch stent that is automatically expanded in the entry duct and the first and second branch ducts when the insertion guide rod is deviated from the insert tube and inserted into the first and second branch ducts is coupled to the stent inserting part, and wherein the insertion guide rod includes: a tubular body part; a first fixing part formed at an outer peripheral surface of the other end of the tubular body part and configured to press and fix the one end of the stent inserting part when the one end of the stent inserting part is inserted into the other end of the tubular body part; and a cover part formed at one end of the tubular body part, and configured to guide insertion of the tubular body part into the first and second branch ducts.

2. The apparatus of claim 1, wherein the insert tube is a tube of a circular shape, a semi-spherical shape, or a polygonal shape.

3. The apparatus of claim 1, wherein the cover part is formed in an inclined structure where a diameter is gradually decreased from a rear end side inserted into the one end of the tubular body part toward a front end side.

4. The apparatus of claim 1, wherein the tubular body part is a tube of a circular shape, a semi-spherical shape, or a polygonal shape.

5. The apparatus of claim 1, wherein the branch stent is coupled to surround the stent inserting part and includes a main stent and first and second branch stents branched from the main stent.

6. The apparatus of claim 5, wherein the first and second branch stents are automatically expanded when deviated from the insert tube from a state of overlapping the insert tube and being pressed therein.

* * * * *